United States Patent
Gerlach et al.

(10) Patent No.: US 7,226,924 B2
(45) Date of Patent: Jun. 5, 2007

(54) SUBSTITUTED 3,4-DIHYDRO-PYRIMIDO [1,2A] PYRIMIDINES AND 3,4-DIHYDRO-PYRAZINO[1,2A]PYRIMIDINES, AND METHODS FOR THEIR PREPARATION AND USE

(75) Inventors: Matthias Gerlach, Brachttal (DE);
Corinna Maul, Aachen (DE);
Utz-Peter Jagusch, Aachen (DE)

(73) Assignee: Gruenenthal GmbH, Aachen (DE)

( * ) Notice: Subject to any disclaimer, the term of this patent is extended or adjusted under 35 U.S.C. 154(b) by 183 days.

(21) Appl. No.: 10/409,614

(22) Filed: Apr. 9, 2003

(65) Prior Publication Data

US 2003/0220322 A1    Nov. 27, 2003

Related U.S. Application Data

(63) Continuation of application No. PCT/EP01/11702, filed on Oct. 10, 2001.

(30) Foreign Application Priority Data

Oct. 13, 2000   (DE)   ................ 100 50 661

(51) Int. Cl.
*C07D 487/04*   (2006.01)
*A61K 31/519*   (2006.01)
*A61P 29/00*   (2006.01)
*A61P 13/02*   (2006.01)

(52) U.S. Cl. ................ 514/249; 544/279; 544/278
(58) Field of Classification Search ............... 544/278, 544/279; 514/249
See application file for complete search history.

(56) References Cited

U.S. PATENT DOCUMENTS

| 3,558,618 | A | 1/1971 | Trepanier et al. |
| 3,887,566 | A * | 6/1975 | Rodway et al. ............... 546/70 |
| 4,219,649 | A | 8/1980 | Knoll et al. |

FOREIGN PATENT DOCUMENTS

| EP | 0329126 | 8/1989 |
| EP | 0 795 555 A1 | 9/1997 |
| WO | 91/13886 | 9/1991 |
| WO | 94/17067 | 8/1994 |

OTHER PUBLICATIONS

Hirots et al., Heterocycles 37(5): 563-570, 1994.*
Mellor et al., Tetrahedron Letters 37(15): 2619-2622, 1996.*
Okamoto et al., Chemical & Pharmaceutical Bulletin 19(4): 764-769, 1971, CA 76:3782, 1972.*
Otomasu et al., Yakugaku Zasshi 90(11): 1391-1395, 1970, CA 77: 126598, 1972.*
"The SMA 12/60 opens the doors to automated biochemical analysis" Journal of Medicinal Chemistry, vol. 11, No. 5, Sep. 1968.

* cited by examiner

*Primary Examiner*—Venkataraman Balasubramanian
(74) *Attorney, Agent, or Firm*—Crowell & Moring LLP

(57) ABSTRACT

Substituted 3,4-dihydro-pyrimido[1,2a]pyrimidines and 3,4-dihydro-pyrazino[1,2a]pyrimidines of general formula I, the invention also relates to a method for the production thereof, substance libraries containing these compounds, medicaments which contain these compounds in the production of medicaments for treating pain, urinary incontinence, itching, tinnitus aurium and/or diarrhea and to pharmaceutical compositions containing these compounds.

18 Claims, No Drawings

SUBSTITUTED 3,4-DIHYDRO-PYRIMIDO[1,2A]PYRIMIDINES AND 3,4-DIHYDRO-PYRAZINO[1,2A]PYRIMIDINES, AND METHODS FOR THEIR PREPARATION AND USE

CROSS REFERENCE TO RELATED APPLICATIONS

The present application is a continuation of International Patent Application No. PCT/EP01/11702, filed Oct. 10, 2001, designating the United States of America and published in German as WO 02/30934 A1, the entire disclosure of which is incorporated herein by reference. Priority is claimed based on Federal Republic of Germany Patent Application No. 100 50 661.5, filed Oct. 13, 2000.

FIELD OF THE INVENTION

The present application relates to substituted 3,4-dihydro-pyrimido[1,2a]pyrimidines and 3,4-dihydro-pyrazino[1,2a]pyrimidines, to methods for their production, to substance libraries containing them, to pharmaceutical preparations which contain these compounds, to the use of these compounds for producing pharmaceutical preparations to treat pain, urinary incontinence, itching, tinnitus aurium and/or diarrhea and to pharmaceutical compositions containing these compounds.

BACKGROUND OF THE INVENTION

The treatment of chronic and non-chronic pain conditions has great importance in medicine. There is a worldwide need for effective therapies for patient-friendly and targeted treatment of chronic and non-chronic pain conditions, especially the successful and satisfactory treatment of pain for the patient.

Conventional opioids, such as morphine, are extremely effective in the treatment of severe to the severest pain. However, their use is limited by known side effects, such as respiratory depression, nausea, sedation, constipation and tolerance development. In addition, they are less effective for neuropathic or incidental pain, from which patients with tumours suffer in particular.

DESCRIPTION OF THE INVENTION

The object of the present invention is to provide analgesically effective compounds which are capable of treating pain, in particular chronic and neuropathic pain. These compounds cause few side effects which opioids with μ-receptor affinity, such as morphine, cause. The side effects include vomiting, nausea, dependency, respiratory depression or constipation.

This object is achieved by the compounds of general formula I which are analgesically effective. The compounds according to the invention are substituted 3,4-dihydro-pyrimido[1,2a]pyrimidines and 3,4-dihydro-pyrazino[1,2a]pyrimidines of general formula I

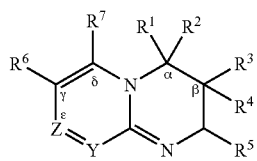

I wherein
Y represents $CR^8$ and
Z represents N; or
Y represents N and
Z represents $CR^9$, $R^1$ and $R^2$ independently of one another are H; $OR^{10}$; SH; $SR^{10}$; $C_{1-12}$ alkyl, wherein alkyl is straight-chained or branched and saturated or unsaturated and unsubstituted or singly or multiply substituted; $C_{3-8}$ cycloalkyl, wherein cycloalkyl is saturated or unsaturated and unsubstituted or singly or multiply substituted; heterocyclyl, wherein heterocyclyl is 3-, 4-, 5-, 6- or 7-membered and is saturated or unsaturated and unsubstituted or singly or multiply substituted; aryl, wherein aryl is unsubstituted or singly or multiply substituted; heteroaryl, wherein heteroaryl is unsubstituted or singly or multiply substituted; ($C_{1-6}$ alkyl)-aryl, wherein $C_{1-6}$ alkyl is straight-chained or branched, saturated or unsaturated, and unsubstituted or singly or multiply substituted, and aryl is unsubstituted or singly or multiply substituted; or ($C_{1-6}$ alkyl)-heteroaryl, wherein $C_{1-6}$ alkyl is straight-chained or branched, saturated or unsaturated, and unsubstituted or singly or multiply substituted, and heteroaryl is unsubstituted or singly or multiply substituted, wherein if one of $R^1$ and $R^2$ is H, and the other of $R^1$ and $R^2$ is not H; and if one of $R^1$ and $R^2$ represents aryl, the other of $R^1$ and $R^2$ represents H or $C_{1-12}$ alkyl, $R^3$ and $R^4$ independently of one another represent H; $C_{1-12}$ alkyl, wherein $C_{1-12}$ alkyl alkyl is straight-chained or branched and saturated or unsaturated and unsubstituted or singly or multiply substituted; $C_{3-8}$ cycloalkyl, wherein cycloalkyl is saturated or unsaturated and unsubstituted or singly or multiply substituted; aryl, wherein aryl is unsubstituted or singly or multiply substituted; heteroaryl, wherein heteroaryl is unsubstituted or singly or multiply substituted; ($C_{1-6}$ alkyl)-aryl, wherein $C_{1-6}$ alkyl is straight-chained or branched and saturated or unsaturated and unsubstituted or singly or multiply substituted, and aryl is unsubstituted or singly or multiply substituted; or ($C_{1-6}$ alkyl)-heteroaryl, wherein $C_{1-6}$ alkyl is straight-chained or branched and saturated or unsaturated and unsubstituted or singly or multiply substituted, and heteroaryl is unsubstituted or singly or multiply substituted, wherein at least one of $R^3$ and $R^4$ is H, or one of $R^1$ or $R^2$ together with one of $R^3$ or $R^4$ forms W, wherein W represents $\alpha'$-$(CH_2)_n$-$\beta$ where n=3, 4, 5, 6, 7, 8, 9 or 10, $\alpha'$-CH=CH—$CH_2$-$\beta'$, $\alpha'$-CH=CH—$CH_2$—$CH_2$-$\beta'$, $\alpha'$-$CH_2$—CH=CH—$CH_2$-$\beta'$, $\alpha'$-$CH_2$—$CH_2$—CH=CH—$CH_2$—$CH_2$-$\beta'$, $\alpha'$-O—$(CH_2)_n$-$\beta$ where n=2, 3, 4, 5 or 6,

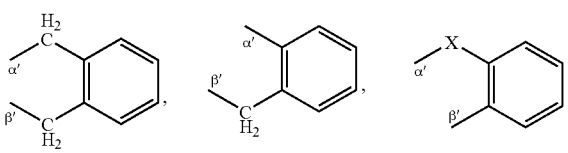

where $X=CH_2$, O or S,

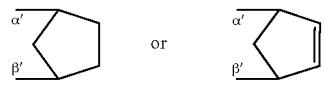

and the end of W denoted by $\alpha'$ is joined to the α-carbon atom of the compound of general formula I and the end of W denoted by β' is joined to the β-carbon atom of the compound of general formula I, the other of $R^1$ and $R^2$ is H or $C_{1-12}$ alkyl, wherein alkyl is straight-chained or branched and saturated or unsaturated and unsubstituted or singly or multiply substituted, and the other of $R^3$ and $R^4$ is H or $C_{1-12}$ alkyl, wherein alkyl is straight-chained or branched and saturated or unsaturated and unsubstituted or singly or multiply substituted, $R^5$ represents $C_{1-12}$ alkyl, wherein $C_{1-12}$ alkyl is straight-chained or branched and saturated or unsaturated and unsubstituted or singly or multiply substituted; $C_{3-8}$ cycloalkyl, wherein cycloalkyl is saturated or unsaturated and unsubstituted or singly or multiply substituted; heterocyclyl, wherein heterocyclyl is 3-, 4-, 5-, 6- or 7-membered and is saturated or unsaturated and unsubstituted or singly or multiply substituted; aryl, wherein aryl is unsubstituted or singly or multiply substituted; heteroaryl, wherein heteroaryl is unsubstituted or singly or multiply substituted; ($C_{1-6}$ alkyl)-aryl, wherein $C_{1-6}$ alkyl is straight-chained or branched and saturated or unsaturated and unsubstituted or singly or multiply substituted, and aryl is unsubstituted or singly or multiply substituted; or ($C_{1-6}$ alkyl)-heteroaryl, wherein $C_{1-6}$ alkyl is straight-chained or branched and saturated or unsaturated and unsubstituted or singly or multiply substituted, and heteroaryl is unsubstituted or singly or multiply substituted, $C(=O)R^{11}$, $CO_2H$ or $CO_2R^{12}$, $R^6$, $R^7$, $R^8$ and $R^9$ independently of one another represent H; F; Cl; Br; I; CN; $NH_2$; $NH(C_{1-6}$ alkyl); $N(C_{1-6}$ alkyl$)_2$; $NH((C_{1-6}$ alkyl)-aryl); $N((C_{1-6}$ alkyl)-aryl$)_2$; NH-aryl; $N(aryl)_2$; $NHR^{13}$; $NO_2$; OH; SH; O—$C_{1-8}$ alkyl or $S(O)_p$—$C_{1-8}$ alkyl, wherein alkyl is straight-chained or branched and saturated or unsaturated and unsubstituted or singly or multiply substituted and p is 0, 1 or 2; O-aryl or $S(O)_q$ aryl, wherein aryl is unsubstituted or singly or multiply substituted and q is 0, 1 or 2, O—($C_{1-6}$ alkyl)-aryl or $S(O)_r$—$C_{1-6}$ alkyl)-aryl, wherein $C_{1-6}$ alkyl is straight-chained or branched and saturated or unsaturated and unsubstituted or singly or multiply substituted, aryl is unsubstituted or singly or multiply substituted, and r is 0, 1 or 2, $CO_2H$, $C(=O)R^{14}$; $C_{1-12}$ alkyl, wherein alkyl is straight-chained or branched and saturated or unsaturated and unsubstituted or singly or multiply substituted; $CF_3$; $C_{3-8}$ cycloalkyl, wherein cycloalkyl is saturated or unsaturated and unsubstituted or singly or multiply substituted; heterocyclyl, wherein heterocyclyl is 3-, 4-, 5-, 6- or 7-membered and is saturated or unsaturated and unsubstituted or singly or multiply substituted, aryl, wherein aryl is unsubstituted or singly or multiply substituted; or heteroaryl, wherein heteroaryl is unsubstituted or singly or multiply substituted, or $R^6$ and $R^7$ together form Q, wherein Q represents γ'-$CR^{15}$=$CR^{16}$—$CR^{17}$=$CR^{18}$-δ', the end of Q denoted by γ' is joined to the γ-carbon atom of the compound of general formula I and the end of Q denoted by δ' is connected to the δ-carbon atom of the compound of general formula I, and Y and Z are as defined above, or $R^6$ and $R^9$ together form T, wherein T represents γ'-$CR^{19}$=$CR^{20}$—$CR^{21}$=$CR^{22}$-ε' or γ'-N=$CR^{20}$—$CR^{21}$=N-ε', the end of T denoted by γ' is joined to the γ-carbon atom of the compound of general formula I and the end of T denoted by ε' is joined to the ε-carbon atom of the compound of general formula I and $R^7$ and $R^8$ are as defined above, $R^{10}$ represents $C_{1-8}$ alkyl, wherein alkyl is straight-chained or branched and saturated or unsaturated and unsubstituted or singly or multiply substituted, $C_{3-8}$ cycloalkyl, wherein cycloalkyl is saturated or unsaturated and unsubstituted or singly or multiply substituted; heterocyclyl, wherein heterocyclyl is 3-, 4-, 5-, 6- or 7-membered and is saturated or unsaturated and unsubstituted or singly or multiply substituted; aryl, wherein aryl is unsubstituted or singly or multiply substituted; heteroaryl, wherein heteroaryl is unsubstituted or singly or multiply substituted; ($C_{1-6}$ alkyl)-aryl, wherein $C_{1-6}$ alkyl is straight-chained or branched and saturated or unsaturated and unsubstituted or singly or multiply substituted and aryl is unsubstituted or singly or multiply substituted; or ($C_{1-6}$ alkyl)-heteroaryl, wherein $C_{1-6}$ alkyl is straight-chained or branched and saturated or unsaturated and unsubstituted or singly or multiply substituted, and heteroaryl is unsubstituted or singly or multiply substituted, $R^{11}$ represents $NH_2$; $NH(C_{1-6}$ alkyl); $N(C_{1-6}$ alkyl$)_2$; $NH((C_{1-6}$ alkyl)-aryl); $N((C_{1-6}$ alkyl)-aryl$)_2$; NH-aryl; $N(aryl)_2$; $C_{1-8}$ alkyl, wherein alkyl is straight-chained or branched and saturated or unsaturated and unsubstituted or singly or multiply substituted; $C_{3-8}$ cycloalkyl, wherein cycloalkyl is saturated or unsaturated and unsubstituted or singly or multiply substituted; aryl, wherein aryl is unsubstituted or singly or multiply substituted; heteroaryl, wherein heteroaryl is unsubstituted or singly or multiply substituted; ($C_{1-6}$ alkyl)-aryl, wherein $C_{1-6}$ alkyl is straight-chained or branched and saturated or unsaturated and unsubstituted or singly or multiply substituted, and aryl is unsubstituted or singly or multiply substituted; or ($C_{1-6}$ alkyl)-heteroaryl, wherein $C_{1-6}$ alkyl is straight-chained or branched and saturated or unsaturated and unsubstituted or singly or multiply substituted and heteroaryl is unsubstituted or singly or multiply substituted, $R^{12}$ represents $C_{1-8}$ alkyl, wherein alkyl is straight-chained or branched and saturated or unsaturated and unsubstituted or singly or multiply substituted; $C_{3-8}$ cycloalkyl, wherein cycloalkyl is saturated or unsaturated and unsubstituted or singly or multiply substituted; ($C_{1-6}$ alkyl)-aryl, wherein $C_{1-6}$ alkyl is straight-chained or branched and saturated or unsaturated and unsubstituted or singly or multiply substituted, and aryl is unsubstituted or singly or multiply substituted, $R^{13}$ represents $C(=O)CH_3$, $C(=O)$ phenyl or $C(=O)O$-t.-butyl(t-BOC), $R^{14}$ represents H; $NH_2$; $NH(C_{1-6}$ alkyl); $N(C_{1-6}$ alkyl$)_2$; $NH((C_{1-6}$ alkyl)-aryl); $N((C_{1-6}$ alkyl)-aryl$)_2$; NH-aryl; $N(aryl)_2$; $C_{1-8}$ alkyl, wherein alkyl is straight-chained or branched and saturated or unsaturated and unsubstituted or singly or multiply substituted, $C_{3-8}$ cycloalkyl, wherein cycloalkyl is saturated or unsaturated and unsubstituted or singly or multiply substituted; aryl; wherein aryl is unsubstituted or singly or multiply substituted; ($C_{1-6}$ alkyl)-aryl, wherein $C_{1-6}$ alkyl is straight-chained or branched and saturated or unsaturated and unsubstituted or singly or multiply substituted, and aryl is unsubstituted or singly or multiply substituted; $OC_{1-8}$ alkyl, wherein alkyl is straight-chained or branched and saturated or unsaturated and unsubstituted or singly or multiply substituted; $OC_{3-8}$ cycloalkyl wherein cycloalkyl is saturated or unsaturated and unsubstituted or singly or multiply substituted; O-aryl, wherein aryl is unsubstituted or singly or multiply substituted; or O—($C_{1-6}$ alkyl)-aryl, wherein $C_{1-6}$ alkyl is straight-chained or branched and saturated or unsaturated and unsubstituted or singly or multiply substituted, and aryl is unsubstituted or singly or multiply substituted, $R^{15}$, $R^{16}$, $R^{17}$ and $R^{18}$ independently of one another represent H, F, Cl, Br, I, OH, CN, $C_{1-8}$ alkyl, wherein alkyl is straight-chained or branched and saturated or unsaturated and unsubstituted or singly or multiply substituted, or $CO_2H$, and $R^{19}$, $R^{20}$, $R^{21}$ and $R^{22}$ independently of one another represent H, F, Cl, Br, I, CN, OH; $C_{1-8}$ alkyl, wherein alkyl is straight-chained or branched and saturated or unsaturated and unsubstituted or singly or multiply substituted, or $CO_2H$, and their pharmaceutically acceptable salts.

The expressions "$C_{1-6}$ alkyl," "$C_{1-8}$ alkyl" and "$C_{1-12}$ alkyl" include, according to this invention, acyclic saturated or unsaturated hydrocarbon radicals which can be branched or straight-chained and unsubstituted or singly or multiply substituted, with respectively 1 to 6, or 1 to 8, or 1 to 12 carbon atoms, i.e. $C_{1-6}$ alkanyls, $C_{2-6}$ alkenyls and $C_{2-6}$ alkinyls or $C_{1-8}$ alkanyls, $C_{2-8}$ alkenyls and $C_{2-8}$ alkinyls or $C_{1-12}$ alkanyls, $C_{2-12}$ alkenyls and $C_{1-12}$ alkinyls. Alkenyls have at least one C—C double bond and alkinyls at least one C—C triple bond. Alkyl is advantageously selected from the group comprising methyl, ethyl, n-propyl, 2-propyl, n-butyl, iso-butyl, sec.-butyl, tert.-butyl, n-pentyl, iso-pentyl, neopentyl, n-hexyl, 2-hexyl, n-octyl, n-decyl, n-dodecyl; ethylenyl (vinyl), ethinyl, propenyl (—$CH_2CH=CH_2$, —CH=CH—$CH_3$, —C(=$CH_2$)—$CH_3$), propinyl (—CH—C≡CH), butenyl, butinyl, pentenyl, pentinyl, hexenyl, hexinyl, octenyl and octinyl.

The expression "$C_{3-8}$ cycloalkyl" represents, for the purposes of this invention, cyclic hydrocarbons with 3 to 8 carbon atoms, which can be saturated or unsaturated, unsubstituted or singly or multiply substituted. $C_{3-8}$ cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl. For the purposes of the present invention cyclopropyl, cyclopropyl-2-carboxylic acid, cyclopropyl-2-carboxylic acid ethyl ester and cyclohexyl are particularly preferred.

The expression "aryl" represents, according to this invention, aromatic hydrocarbons, inter alia phenyls, naphthyls and anthracenyls. The aryl radicals can also be condensed with further saturated, unsaturated or partially unsaturated or aromatic ring systems. Each aryl radical may be present in an unsubstituted or singly or multiply substituted form, wherein the aryl substituents may be the same or different and in any position of the aryl. Aryl is advantageously selected from the group comprising phenyl, 1-naphthyl and 2-naphthyl. For the purposes of this invention particularly preferred aryl radicals are m-toluyl, p-hydroxy-phenyl, p-methoxyphenyl, 4-hydroxy-3-methoxyphenyl, 3,4-dimethoxyphenyl, 2,4-dimethylphenyl, 4-fluorophenyl, 1-naphthyl and 2-naphthyl.

The expression "heteroaryl" represents a 5-, 6- or 7-membered cyclic aromatic radical which contains at least 1, 2, 3, 4 or 5 heteroatoms, wherein the heteroatoms may be the same or different and the heterocycle can be unsubstituted or singly or multiply substituted; in the case of substitution on the heterocycle the heteroaryl substituents may be the same or different and in any position of the heteroaryl. The heterocycle can also be part of a bi- or polycyclic system. Preferred heteroatoms are nitrogen, oxygen and sulphur. It is preferred if the heteroaryl radical is selected from the group comprising pyrrolyl, indolyl, furyl (furanyl), benzofuranyl, thienyl (thiophenyl), benzothienyl, pyrazolyl, imidazolyl, thiazolyl, oxazolyl, isoxazoyl, pyridinyl, pyridazinyl, pyrimidinyl, pyrazinyl, pyranyl, indolyl, indazolyl, purinyl, pyrimidinyl, indolizinyl, quinolinyl, isoquinolinyl, quinazolinyl, carbazolyl, phenazinyl, phenothiazinyl, wherein the bond with the compounds of general formula I can be made by any arbitrary and possible ring member of the heteroaryl radical. For the purposes of this invention particularly preferred heteroaryl radicals are pyridin-2-yl, furan-2-yl, 5-methyl-furan-2-yl and 5-nitro-furan-2-yl.

The expressions "($C_{1-6}$ alkyl)-aryl" and "($C_{1-6}$ alkyl)-heteroaryl," for the purposes of the present invention, mean that $C_{1-6}$ alkyl, aryl and heteroaryl have the meanings defined above and are bound by a $C_{1-6}$ alkyl group to the compound of general formula I.

The expression "heterocyclyl" represents a 3-, 4-, 5-, 6- or 7-membered cyclic organic radical containing at least 1, possibly also 2, 3, 4 or 5 heteroatoms, wherein the heteroatoms may be the same or different and the cyclic radical can be saturated or unsaturated, but is not aromatic, and can be unsubstituted or singly or multiply substituted. The heterocycle can also be part of a bi- or polycyclic system. Preferred heteroatoms are nitrogen, oxygen and sulphur. It is preferred if the heterocyclyl radical is selected from the group comprising tetrahydrofuryl, tetrahydropyranyl, pyrrolidinyl, piperidinyl, piperazinyl and morpholinyl, wherein the bond with the compound of general formula I (or II, III or IV) can be made by any ring member of the heterocyclyl radical.

In conjunction with "alkyl," "alkanyl," "alkenyl" and "alkinyl," the term "substituted" is taken to mean, according to this invention, the substitution of a hydrogen radical by F, Cl, Br, I, CN, $NH_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, $NO_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-heterocyclyl, C(=S)-heterocyclyl, $CO_2H$, $CO_2$-alkyl, C(=O)$NH_2$, C(=O)NH-alkyl, C(=O)NH-aryl, C(=O)NH-heterocyclyl, C(=O)N(alkyl)$_2$, C(=O)N(alkyl-aryl)$_2$, C(=O)N(alkyl-heteroaryl)$_2$, C(=O)N(heterocyclyl)$_2$, SO-alkyl, $SO_2$-alkyl, $SO_2NH_2$, $SO_3H$, cycloalkyl, aryl, heteroaryl or heterocyclyl, wherein multiply substituted radicals are taken to mean those radicals which are substituted either on different atoms or multiply on the same atoms, for example twice or three times, for example three times on the same carbon atom as in the case of $CF_3$ or —$CH_2CF_3$, or at various positions as in the case of —CH(OH)—CH=CH—$CHCl_2$. Multiple substitution can be made with the same or with different substituents. For the purposes of the present invention alkyl particularly preferably represents methyl, ethyl, $CH_2$—$CH_2$—OH or $CF_3$.

With respect to "aryl," "alkyl-aryl," "heteroaryl," "alkyl-heteroaryl," "heterocyclyl" and "cycloalkyl," according to this invention "singly or multiply substituted" is taken to mean the single or multiple, for example double, triple or fourfold, substitution of one or more hydrogen atoms of the ring system by F; Cl, Br, I, CN, $NH_2$, NH-alkyl, NH-aryl, NH-heteroaryl, NH-alkyl-aryl, NH-alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, NO, $NO_2$, SH, S-alkyl, S-cycloalkyl, S-aryl, S-heteroaryl, S-alkyl-aryl, S-alkyl-heteroaryl, S-heterocyclyl, S-alkyl-OH, S-alkyl-SH, OH, O-alkyl, O-cycloalkyl, O-aryl, O-heteroaryl, O-alkyl-aryl, O-alkyl-heteroaryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S) $C_{1-6}$-alkyl-aryl, C(=O)-heteroaryl, C(=S)-heteroaryl, C(=O)-heterocyclyl, C(=S)-heterocyclyl, $CO_2H$, $CO_2$-alkyl, C(=O)NH2, C(=O)NH-alkyl, C(=O)NH-aryl, C(=O)NH-heterocyclyl, C(=O)N(alkyl)$_2$, C(=O)N(alkyl-aryl)$_2$, C(=O)N(alkyl-heteroaryl)$_2$, C(=O)N(heterocyclyl)$_2$, S(O)-alkyl, S(O)-aryl, $SO_2$-alkyl, $SO_2$-aryl, $SO_2NH_2$, $SO_3H$, cycloalkyl, aryl, heteroaryl, $CF_3$, =O, =S; $C_{1-6}$-alkanyl, $C_{2-6}$-alkenyl, $C_{2-6}$-alkinyl, —$C_{1-6}$-alkyl-C(O)O—$C_{1-6}$-alkyl; phenyl, benzyl, naphthyl and/or heterocyclyl; on one or possibly more atoms (wherein one substituent can, in turn, possibly be substituted). The multiple substitution is made here with the same or with different substituents. Particularly preferred substituents for "aryl" are OH, F, $CH_3$ and O—$CH_3$. Particularly preferred substituents for "heteroaryl" are $CH_3$ and $NO_2$. Particularly preferred substituents for "cycloalkyl" are $CO_2H$ and $CO_2$ ethyl.

Pharmaceutically acceptable salts according to this invention are those salts of the compounds according to the invention in accordance with general formula I which are physiologically acceptable for pharmaceutical use, in particular when applied to humans or other mammals. Pharmaceutically acceptable salts of this type can, for example, be formed with inorganic or organic acids.

The pharmaceutically acceptable salts of the compounds according to the invention in accordance with general formula I are preferably formed with hydrochloric acid, hydrobromic acid, sulphuric acid, phosphoric acid, methane sulphonic acid, p-toluene sulphonic acid, carbonic acid, formic acid, acetic acid, oxalic acid, succinic acid, tartaric acid, mandelic acid, fumaric acid, lactic acid, citric acid, glutamic acid or aspartic acid. The salts formed are inter alia hydrochlorides, hydrobromides, phosphates, carbonates, hydrogen carbonates, formates, acetates, oxalates, succinates, tartrates, fumarates, citrates and glutaminates. The hydrates of the compounds according to the invention which, for example, can be obtained from aqueous solution by crystallisation, are also preferred.

All compounds according to the invention contain at least one asymmetric center, namely the carbon atom of structure I substituted by $R^5$. Therefore, the compounds according to the invention of general formula I can be present in the form of their racemates, in the form of the pure enantiomers and/or diastereomers or in the form of mixtures of these enantiomers or diastereomers, and, more precisely, both in the form depicted and as pharmaceutically acceptable salts of these compounds. The mixture can be present in any mixing ratio of the stereoisomers. The compounds of general formula I are preferably present as enantiomer-pure compounds.

A group of preferred compounds of the present invention is formed by 3,4-dihydro-pyrimido[1,2a]pyrimidines, i.e. compounds of general formula I, where Y=N and Z=$CR^9$, in which one of the radicals $R^1$ and $R^2$ represents $OR^{10}$, $SR^{10}$, $C_{1-6}$ alkyl or aryl, one of the radicals $R^3$ and $R^4$ represents H or $C_{1-6}$ alkyl, or one of the radicals $R^1$ and $R^2$ together with one of the radicals $R^3$ and $R^4$ forms W, wherein W represents α'-CH=CH—$CH_2$—$CH_2$-β',

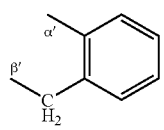

or

and the two other radicals from $R^1$, $R^2$, $R^3$ and $R^4$ represents H or $C_{1-12}$ alkyl, $R^5$ represents $C_{3-7}$ cycloalkyl, heteroaryl, $C(=O)R^{11}$, $CO_2H$ or $CO_2R^{12}$, $R^6$ represents H, F, Cl, Br, CN, $NO_2$, $C(=O)R^{14}$, $C_{1-6}$ alkyl, $CF_3$ or aryl, $R^7$ represents H, F, Cl, Br, CN, $NH_2$, OH or $C_{1-6}$ alkyl, $R^9$ represents H, OH, $CF_3$ or $C_{1-6}$ alkyl or $R^6$ and $R^9$ together form T, wherein T represents γ'-N=$CR^{20}$—$CR^{21}$=N-ε', $R^{10}$ represents $C_{1-8}$ alkyl or aryl, $R^{11}$ represents aryl, $R^{12}$ represents $C_{1-6}$ alkyl, $R^{14}$ represents $OC_{1-6}$ alkyl, $R^{20}$ represents H or $CH_2H$ and $R^{21}$ represents H.

Particularly preferred compounds of this group are 3,4-dihydro-pyrimido[1,2a]pyrimidines of general formula IA

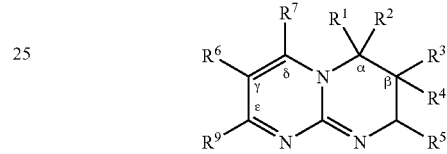

IA in which one of the radicals $R^1$ and $R^2$ represents O—$(CH_2)_2$—OH, S-phenyl, phenyl, 3-methylphenyl, 2,4-dimethylphenyl, 4-hydroxyphenyl, 4-methoxyphenyl, 4-hydroxy-3-methoxyphenyl, 3,4-dimethoxyphenyl or 2-naphthyl, one of the radicals $R^3$ and $R^4$ represents H or methyl, or one of the radicals $R^1$ and $R^2$ together with one of the radicals $R^3$ and $R^4$ forms W, wherein W represents α'-CH=CH—$CH_2$—$CH_2$-β',

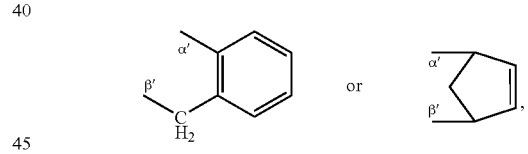 or 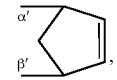, and the two other radicals from $R^1$, $R^2$, $R^3$ and $R^4$ represent H, $R^5$ represents cyclopropyl, 2-(C(=O)O-ethyl)-cyclopropyl, cyclohexyl, 2-pyridinyl, C(=O) phenyl, $CO_2H$ or $CO_2$ ethyl, $R^6$ represents H, Br, $CO_2$ ethyl or methyl, $R^7$ represents H, $NH_2$, OH or methyl and $R^9$ represents H, Cl, OH or $CF_3$ or $R^6$ and $R^9$ together form T, wherein T represents γ'-N=$C(CO_2H)$—CH=N-ε'.

Preferred dihydro-pyrimido[1,2a]pyrimidines according to the invention of general formula IA are those which are selected from:
7-bromo-4-(4-methoxy-phenyl)-3,4-dihydro-2H-pyrimido[1,2a]pyrimidine-2-carboxylic acid ethyl ester,
7-bromo-4-(3,4-dimethoxy-phenyl)-3,4-dihydro-2H-pyrimido[1,2a]pyrimidine-2-carboxylic acid,
7-bromo-4-(4-methoxy-phenyl)-3,4-dihydro-2H-pyrimido[1,2a]pyrimidine-2-carboxylic acid,
7-bromo-4-(4-hydroxy-phenyl)-3-methyl-3,4-dihydro-2H-pyrimido[1,2-a]pyrimidine-2-carboxylic acid ethyl ester,
2-bromo-6,6a,7,11b-tetrahydro-4,5,11c-triaza-benzo[c]fluorene-6-carboxylic acid ethyl ester, 7-bromo-4-(4-methoxy-phenyl)-3-methyl-3,4-dihydro-2H-pyrimido[12a]pyrimidine-2-carboxylic acid, 7-bromo-4-(3,4-dimethoxy-phenyl)-3,4-dihydro-2H-pyrimido[1,2a]pyrimidine-2-carboxylic acid, 7-bromo-4-(4-methoxy-phenyl)-3,4-dihydro-2H-pyrimido[1,2a]pyrimidine-2-carboxylic acid,

[7-bromo-4-(2-hydroxy-ethoxy)-3,4-dihydro-2H-pyrimido[1,2a]pyrimidin-2-yl]-phenyl-methanone,

[7-bromo-4-(4-hydroxy-3-methoxy-phenyl)-3-methyl-3,4-dihydro-2H-pyrimido[1,2a]pyrimidin-2-yl]-phenyl-methanone,

[7-bromo-4-(4-methoxy-phenyl)-3-methyl-3,4-dihydro-2H-pyrimido[1,2a]pyrimidin-2-yl]-phenyl-methanone,

[7-bromo-4-(4-hydroxy-phenyl)-3-methyl-3,4-dihydro-2H-pyrimido[1,2-a]pyrimidin-2-yl]-phenyl-methanone,

[7-bromo-4-(3,4-dimethoxy-phenyl)-3,4-dihydro-2H-pyrimido[1,2a]pyrimidin-2-yl]-phenyl-methanone,

[7-bromo-4-(4-methoxy-phenyl)-3,4-dihydro-2H-pyrimido[1,2a]pyrimidin-2-yl]-phenyl-methanone, 2-(7-bromo-2-cyclopropyl-3,4-dihydro-2H-pyrimido[1,2a]pyrimidin-4yloxy)-ethanol, 2-(7-bromo-2-cyclohexyl-3,4-dihydro-2H-pyrimido[1,2a]pyrimidin-4yloxy)-ethanol, 4-(7-bromo-2-cyclohexyl-3-methyl-3,4-dihydro-2H-pyrimido[1,2a]pyrimidin-4-yl)-phenol, 7-bromo-4-naphthalen-2-yl-3,4-dihydro-2H-pyrimido[1,2a]pyrimidine-2-carboxylic acid ethyl ester, 7-bromo-4-m-tolyl-3,4-dihydro-2H-pyrimido[1,2a]pyrimidine-2 carboxylic acid ethyl ester, 2-[7-bromo-4-(2,4-dimethyl-phenyl)-3,4-dihydro-2H-pyrimido[1,2a]pyrimidin-2-yl]-cyclopropane carboxylic acid ethyl ester, 2-[7-bromo-4-(4-methoxy-phenyl)-3,4-dihydro-2H-pyrimido[1,2a]pyrimidin-2-yl]-cyclopropane carboxylic acid ethyl ester, 7-bromo-4-phenylsulphanyl-2-pyridin-2-yl-3,4-dihydro-2H-pyrimido[1,2-a]pyrimidine, 2-chloro-6-phenylsulphanyl-8-pyridin-2-yl-7,8-dihydro-6H-pyrimido[1,2-a]pyrimidin-4-yl-amine, 6-phenylsulphanyl-8-pyridin-2-yl-7,8-dihydro-6H-pyrimido[1,220 a]pyrimidine-2,4-diol, 6-phenylsulphanyl-8-pyridin-2-yl-2-trifluoromethyl-7,8-dihydro-6H-pyrimido[1,2a]pyrimidine-3-carboxylic acid ethyl ester, 3-methyl-5,8-methano-9-pyridin-2-yl-5,8,8a,9-tetrahydro-4bH-1,4a,10-triaza-phenanthrene-2,4-diol, 5,8-methano-9-pyridin-2-yl-5,8,8a,9-tetrahydro-4bH-1,4a,10-triazaphenanthrene-2,4-diol, 12-hydroxyl-1,4-methano-5-pyridin-2-yl-1,4a,5,12b-tetrahydro-4H-6,7,8,11,12a-pentaaza-benzo[a]anthracene-10-carboxylic acid, and 3-bromo-9-pyridin-2-yl-7,8,8a,9-tetrahydro-4bH-1,4a,10-triaza-phenanthrene, and their pharmaceutically acceptable salts.

A further group of preferred compounds is formed by 3,4-dihydro-pyrazino[1,2a]pyrimidines, i.e. compounds of general formula I, where $Y=CR^8$ and $Z=N$, in which one of the radicals $R^1$ and $R^2$ represent $OR^{10}$, $SR^{10}$, $C_{1-6}$ alkyl or aryl, one of the radicals $R^3$ and $R^4$ represents H or $C_{1-6}$ alkyl, or one of the radicals $R^1$ and $R^2$ together with one of the radicals $R^3$ and $R^4$ form W, wherein W represents

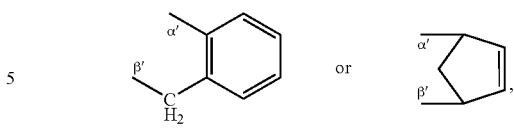

and the two other radicals from $R^1$, $R^2$, $R^3$ and $R^4$ represent H or $C_{1-12}$ alkyl, $R^5$ represents $C_{3-7}$ cycloalkyl, heteroaryl, $C(=O)R^{11}$, $CO_2H$ or $CO_2R^{12}$, $R^6$ represents H, F, Cl, Br, CN, $NO_2$, $C(=O)R^{14}$, $C_{1-6}$ alkyl, $CF_3$ or aryl, $R^7$ represents H, F, Cl, Br, CN, $NH_2$, OH or $C_{1-6}$ alkyl, $R^8$ represents H, F, Cl, Br, CN, $NO_2$, O—$(C_{1-6}$ alkyl)-aryl, $CO_2H$, $CONH_2$ or $C_{1-6}$ alkyl, $R^{10}$ represents $C_{1-8}$ alkyl or aryl, $R^{11}$ represents aryl, $R^{12}$ represents $C_{1-6}$ alkyl and $R^{14}$ represents $OC_{1-6}$ alkyl. These compounds can also be present in the form of one of their pharmaceutically acceptable salts.

Particularly preferred compounds of this group are 3,4-dihydro-pyrazino[1,2a]pyrimidines of general formula IB

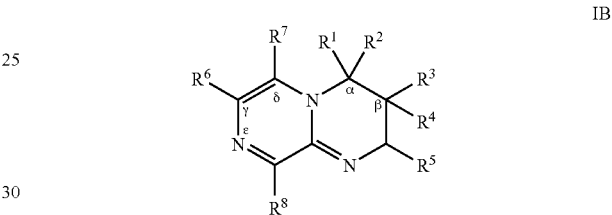

in which one of the radicals $R^1$ and $R^2$ represent O—$(CH_2)_2$—OH, S-phenyl, methyl, phenyl, 2,4-dimethylphenyl, 4-hydroxyphenyl, 4-methoxyphenyl, 4-hydroxy-3-methoxyphenyl or 3,4-dimethoxyphenyl, one of the radicals $R^3$ and $R^4$ represents H or methyl, or one of the radicals $R^1$ and $R^2$ together with one of the radicals $R^3$ and $R^4$ forms W, wherein W represents

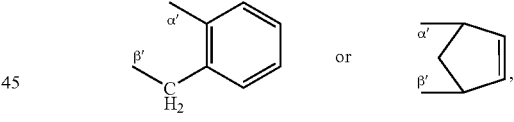

and the two other radicals from $R^1$, $R^2$, $R^3$ and $R^4$ represent H, $R^5$ represents cyclopropyl, 2-(C(=O)O-ethyl)-cyclopropyl, cyclohexyl, 2-pyridinyl, 5-methyl-furan-2-yl, 5-nitro-furan-2-yl, C(=O) phenyl, $CO_2H$ or $CO_2$ ethyl, $R^6$ represents H, Cl, CN or phenyl, $R^7$ represents H, $NH_2$ or CN and $R^8$ represents H, Cl, CN, $CO_2H$ or $CONH_2$, and their pharmaceutically acceptable salts.

Preferred dihydro-pyrazino[1,2a]pyrimidines according to the invention of general formula IB are those which are selected from:

4-(4-methoxy-phenyl)-3-methyl-2-(5-nitro-furan-2-yl)-3,4-dihydro-2H-pyrazino[1,2a]pyrimidine, 2-[4-(4-methoxy-phenyl)-3-methyl-3,4-dihydro-2H-pyrazino[1,2a]pyrimidin-2-yl]-cyclopropane carboxylic acid ethyl ester, 4-(4-methoxy-phenyl)-3-methyl-2-(5-methyl-furan-2-yl)-3,4-dihydro-2H-pyrazino[1,2a]pyrimidine, 4-(3,4-dimethoxy-phenyl)-3,4-dihydro-2H-pyrazino[1,2a]pyrimidine-2-carboxylic acid ethyl ester, 4-(4-methoxy-phenyl)-3,4-dihydro-2H-pyrazino[1,2a]pyrimidine-2-carboxylic acid ethyl ester,
4-(3,4-dimethoxy-phenyl)-3,4-dihydro-2H-pyrazino[1,2a]pyrimidine-2-carboxylic acid,
4-(4-methoxy-phenyl)-3,4-dihydro-2H-pyrazino[1,2a]pyrimidine-2-carboxylic acid,
4-(4-methoxy-phenyl)-2-(5-nitro-furan-2-yl)-3,4-dihydro-2H-pyrazino[1,2a]pyrimidine,
2-[4-(2,4-dimethyl-phenyl)-3,4-dihydro-2H-pyrazino[1,2a]pyrimidin-2-yl]-cyclopropane carboxylic acid ethyl ester,
2-[4-(4-methoxy-phenyl)-3,4-dihydro-2H-pyrazino[1,2a]pyrimidin-2-yl]-cyclopropane carboxylic acid ethyl ester,
4-(4-hydroxy-phenyl)-3-methyl-3,4-dihydro-2H-pyrazino[1,2a]pyrimidine-2-carboxylic acid ethyl ester,
6,6a,7,11b-tetrahydro-3,5,11c-triaza-benzo[c]fluorene-6-carboxylic acid ethyl ester,
4-phenylsulphanyl-3,4-dihydro-2H-pyrazino[1,2a]pyrimidine-2-carboxylic acid ethyl ester,
4-phenylsulphanyl-3,4-dihydro-2H-pyrazino[1,2a]pyrimidine-2-carboxylic acid,
4-(4-methoxy-phenyl)-3-methyl-3,4-dihydro-2H-pyrazino[1,2a]pyrimidine-2-carboxylic acid,
4-(3,4-dimethoxy-phenyl)-3,4-dihydro-2H-pyrazino[1,2a]pyrimidine-2-carboxylic acid,
4-(4-methoxy-phenyl)-3,4-dihydro-2H-pyrazino[1,2a]pyrimidine-2-carboxylic acid,
[4-(2-hydroxy-ethoxy)-3,4-dihydro-2H-pyrazino[1,2a]pyrimidin-2-yl]phenyl-methanone,
[4-(4-hydroxy-3-methoxy-phenyl)-3-methyl-3,4-dihydro-2H-pyrazino[1,2a]pyrimidin-2-yl]-phenyl-methanone,
[4-(4-methoxy-phenyl)-3-methyl-3,4-dihydro-2H-pyrazino[1,2a]pyrimidin-2-yl]-phenyl-methanone,
[4-(4-hydroxy-phenyl)-3-methyl-3,4-dihydro-2H-pyrazino[1,2a]pyrimidin-2-yl]-phenyl-methanone,
2-cyclopropyl-4-(3,4-dimethoxy-phenyl)-3,4-dihydro-2H-pyrazino[1,2-a]pyrimidine,
2-cyclopropyl-4-(4-methoxy-phenyl)-3,4-dihydro-2H-pyrazino[1,2a]pyrimidine,
2-(2-cyclohexyl-3,4-dihydro-2H-pyrazino[1,2a]pyrimidin-4-yloxy)ethanol,
2-cyclohexyl-4-(4-methoxy-phenyl)-3,4-dihydro-2H-pyrazino[1,2a]pyrimidine,
4-methyl-2-(5-nitro-furan-2-yl)-4-phenyl-3,4-dihydro-2H-pyrazino[1,2-a]pyrimidine,
2-(4-methyl-4-phenyl-3,4-dihydro-2H-pyrazino[1,2a]pyrimidin-2-yl)-cyclopropane carboxylic acid ethyl ester,
4-phenyl-2-pyridin-2-yl-3,4-dihydro-2H-pyrazino[1,2a]pyrimidine,
4-phenyl-2-pyridin-2-yl-3,4-dihydro-2H-pyrazino[1,2a]pyrimidine-9-carboxylic acid,
6-amino-7-chloro-4-phenyl-2-pyridin-2-yl-3,4-dihydro-2H-pyrazino[1,2-a]pyrimidine-9-carboxylic acid amide,
2-phenylsulphanyl-3-pyridin-2-yl-2,3-dihydro-1H-pyrimido[1,2a]quinolin-10-ol,
4-phenylsulphanyl-2-pyridin-2-yl-3,4-dihydro-2H-pyrazino[1,2a]pyrimidine-9-carboxylic acid,
6-amino-7-chloro-4-phenylsulphanyl-2-pyridin-2-yl-3,4-dihydro-2H-pyrazino[1,2a]pyrimidine-9-carboxylic acid amide,
7-phenyl-4-phenylsulphanyl-2-pyridin-2-yl-3,4-.dihydro-2H-pyrazino[1,2a]pyrimidine-9-carbonitrile, and
5,8-methano-9-pyridin-2-yl-5,8,8a,9-tetrahydro-4bH-2,4a,10-triazaphenanthrene,
1-chloro-5,8-methano-9-pyridin-2-yl-5,8,8a,9-tetrahydro-4bH-2,4a, 10-triaza-phenanthrene-3,4-dicarbonitrile, and their pharmaceutically acceptable salts.

The invention also relates to a method for producing the compounds of structure I and their pharmaceutically acceptable salts.

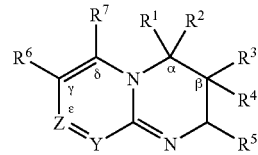

I wherein Y, Z and $R^1$ to $R^7$ are as defined above.

The method of the invention comprises
a heteroarylamine of general formula II

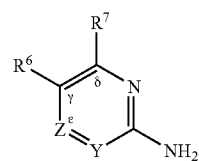

II wherein Y, Z, $R^6$ and $R^7$ are as defined above, with the proviso that if $R^6$ and $R^7$ form Q as defined above, the end of Q denoted by γ' is joined to the γ-carbon atom of the heteroarylamine of general formula II and the end of Q denoted by δ' is joined to the δ-carbon atom of the heteroarylamine of general formula II, and that if $R^6$ and $R^9$ form T as defined above, the end denoted by γ' is joined to the γ-carbon atom of the heteroarylamine of general formula II and the end denoted by ε' is joined to the ε-carbon atom of the heteroarylamine of general formula II, is reacted with an aldehyde of general formula III

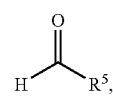

III wherein $R^5$ is as defined above,
and with an olefin of general formula IV

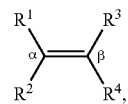

IV wherein $R^1$, $R^2$, $R^3$ and $R^4$ are as defined above, with the proviso that if one of the radicals $R^1$ and $R^2$ together with one of the radicals $R^3$ and $R^4$ forms W, the end of W denoted by α' is joined to the α-carbon atom of the olefin of general formula IV and the end of W denoted by β' is joined to the β-carbon atom of the olefin of general formula IV, in the presence of an acid.

Heteroarylamines of general formula IIA

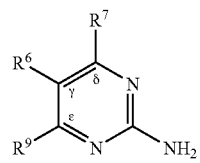

wherein $R^6$, $R^7$ and $R^9$ are as defined above for formula II, are used to produce the 3,4-dihydro-pyrimido[1,2a]pyrimidines according to the invention of general formula IA in the method according to the invention.

To produce the 3,4-dihydro-pyrazino[1,2a]pyrimidines according to the invention of general formula IB, heteroarylamines of general formula IIB

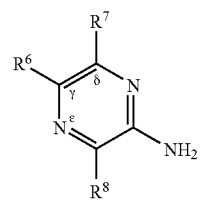

wherein $R^6$ to $R^8$ are as defined above for formula II, are used in the method according to the invention.

The method according to the invention is preferably carried out in a "one pot" reaction in which a respective heteroarylamine of general formula II, a respective aldehyde of general formula III and a respective olefin of general formula IV are simultaneously reacted with one another.

The method according to the invention can also be carried out in semi- or fully-automated form as a parallel synthesis of a group of compounds according to the invention of general formula I.

The acid used is an inorganic or organic proton acid or Lewis acid. The reaction is preferably carried out in the presence of an organic acid, for example acetic acid, methane sulphonic acid or, in particular, trifluoroacetic acid.

The production method according to the invention can be carried out in any suitable solvent in which the reactants sufficiently dissolve. Organic solvents, for example dichloromethane or, in particular, acetonitrile are preferred as solvents.

The compounds according to the invention of general formula I are expediently produced according to the invention at a temperature of 0 to 100° C., in particular at 15 to 40° C. The reaction time is preferably 15 minutes to 12 hours and can be adapted to the respective requirements.

The heteroarylamines of general formula II, the aldehydes of general formula III and the olefins of general formula IV used in the method according to the invention are commercially available (from Acros, Geel; Avocado, Port of Heysham; Aldrich, Deisenhofen; Fluka, Seelze; Lancaster; Mülheim; Maybridge, Tintagel; Merck, Darmstadt; Sigma, Deisenhofen; TCI, Japan) or can be produced by methods generally known in the prior art.

The compounds according to the invention of general formula I can be isolated both as a free base and as a salt. The free base of the compound of general formula I is conventionally obtained after the reaction by the method according to the invention described above and subsequent conventional working up. The base obtained in this way can then be converted into the corresponding salt, for example by reaction with an inorganic or organic acid, preferably with hydrochloric acid, hydrobromic acid, sulphuric acid, phosphoric acid, methane sulphonic acid, p-toluene sulphonic acid, carbonic acid, formic acid, acetic acid, oxalic acid, succinic acid, tartaric acid, mandelic acid, fumaric acid, lactic acid, citric acid, glutamic acid or aspartic acid. The salts formed are inter alia hydrochlorides, hydrobromides, phosphates, carbonates, hydrogen carbonates, formates, acetates, oxalates, succinates, tartrates, fumarates, citrates and glutaminates. The particularly preferred hydrochloride formation can also be brought about by reacting the base dissolved in a suitable organic solvent with trimethylsilyl chloride (TMSCl).

If the compounds of general formula I are obtained as racemates or as mixtures of their various enantiomers and/or diasteriomers in the production method according to the invention, these mixtures can be separated by methods well known in the art. Suitable methods are inter alia chromatographic methods of separation, in particular liquid chromatography methods under normal and elevated pressure, preferably MPLC and HPLC methods, and methods of fractional crystallisation. In particular individual enantiomers can be separated from one another, for example by means of HPLC on the chiral phase or by crystallisation of diastereomeric salts formed with chiral acids, for instance (+)-tartaric acid, (−)-tartaric acid or (+)-10-camphoric sulphonic acid.

The present invention also relates to a substance library containing at least one compound of general formula I as defined above. The substance library according to the invention preferably contains at least 15 and, in particular at least 30, compounds of general formula I.

For the purposes of the present invention a "substance library" is taken to mean a group of compounds which are produced by the same method under the same or virtually the same reaction conditions and with variation of a reagent or a plurality of reagents. A substance library of this type can contain the library members both as individual pure compounds and as a mixture of these compounds. Medical screening by one or more in vitro screening methods, for example, may be carried out in automated form with the aid of this substance library.

The compounds according to the invention have proven to be analgesically effective. Therefore, the present invention also relates to a pharmaceutical preparation containing at least one of the compounds according to the invention and as defined above, of general formula I or one of their pharmaceutically acceptable salts. The compounds according to the invention can be present in the pharmaceutical preparation according to the invention as a pure isomer, in particular a pure enantiomer or a pure diastereomer but also as a racemic or non-racemic mixture. It is preferred that the pharmaceutical preparation contains a pharmaceutically acceptable salt of the compounds according to the invention, in particular a hydrochloride.

The invention also relates to the use of at least one compound according to the invention of general formula I, including its diasteriomers or enantiomers, also as racemates or an enantiomer mixture in the form of its free base or a salt formed with a physiologically acceptable acid, in particular the hydrochloride salt, to produce a pharmaceutical preparation for treating pain.

It has surprisingly been found that the compounds according to the invention of general formula I are very suitable for further indications, in particular for treating urinary incontinence, itching, tinnitus aurium and/or diarrhea. The invention therefore also relates to the use of at least one compound according to the invention of general formula I, including a pharmaceutically acceptable salt, to produce a pharmaceutical preparation for treating urinary incontinence, itching, tinnitus aurium and/or diarrhea.

Furthermore, the present invention also relates to pharmaceutical compositions containing at least one compound of general formula I as defined above or one of its pharmaceutically acceptable salts and one or more pharmaceutical auxiliaries.

The pharmaceutical preparations and compositions according to the invention can be present in liquid, semi-solid or solid dosage forms and in the form of, for example injection solutions, drops, liquids, syrups, sprays, suspensions, granules, tablets, pellets, transdermal therapeutic systems, capsules, plasters, suppositories, ointments, creams, lotions, gels, emulsions or aerosols and, in addition to at least one compound according to the invention of general formula I, contain pharmaceutical auxiliaries such as excipients, fillers, solvents, diluents, surface-active substances, dyes, preservatives, exploding agents, lubricants, flavourings and/or binders depending on the galenic form. These auxiliaries can, for example, be: water, ethanol, 2-propanol, glycerol, ethylene glycol, propylene glycol, polyethylene glycol, polypropylene glycol, glucose, fructose, lactose, saccharose, dextrose, molasses, starch, modified starch, gelatines, sorbitol, inositol, mannitol, microcrystalline cellulose, methyl cellulose, carboxylmethyl cellulose, cellulose acetate, shellac, cetyl alcohol, polyvinylpyrrolidone, paraffins, waxes, natural and synthetic rubbers, acacia gum, alginates, dextran, saturated and unsaturated fatty acids, stearic acid, magnesium stearate, zinc stearate, glyceryl stearate, sodium lauryl sulphate, edible oils, sesame oil, coconut oil, peanut oil, soya bean oil, lecithin, sodium lactate, polyoxyethylene and polyoxypropylene fatty acid ester, sorbitan fatty acid ester, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talc, kaolin, pectin, crospovidon, agar and bentonite.

The choice of auxiliaries and the amount thereof to be used depends on whether the pharmaceutical preparation is to be applied orally, subcutaneously, parenterally, intravenously, vaginally, pulmonally, intraperitoneally, transdermally, intramuscularly, nasally, buccally, rectally or topically, for example to infections of the skin, the mucous membranes or the eyes. Preparations in the form of tablets, dragees, capsules, granules, drops, liquids and syrups inter alia are suitable for oral application, solutions, suspensions, easily reconstitutable powders for inhalation and sprays inter alia are suitable for parenteral, topical and inhalative application. Compounds according to the invention of general formula I in a deposit in dissolved form or in a plaster, optionally with the addition of substances promoting skin penetration, are suitable percutaneous application preparations. Rectally, transmucosally, parenterally, orally or percutaneously applicable preparation forms can release the compounds according to the invention of general formula I with a delay.

The pharmaceutical preparations and compositions according to the invention are produced with the aid of agents, devices, methods and processes well known in the art of pharmaceutical formulation, as described, for example, in "Remington's Pharmaceutical Sciences," Editor A. R. Gennaro, 17th Edition, Mack Publishing Company, Easton, Pa. (1985) in particular in Part 8, Chapters 76 to 93.

Therefore, for example, a solid formulation, such as a tablet, the active ingredient of the pharmaceutical preparation, i.e. a compound of general formula I or one of its pharmaceutically acceptable salts, can be granulated with a pharmaceutical excipient, for example conventional tablet ingredients, such as corn starch, lactose, saccharose, sorbitol, talc, magnesium stearate, dicalcium phosphate or pharmaceutically acceptable rubbers, and pharmaceutical diluents, such as water, in order to form a solid composition containing a compound according to the invention or a pharmaceutically acceptable salt thereof in a homogeneous distribution. A homogeneous distribution here is taken to mean that the active ingredient is uniformly distributed over the entire composition so it can be readily subdivided into uniformly acting single dose forms, such as tablets, pills or capsules. The solid composition is then subdivided into single dose forms. The tablets or pills of the pharmaceutical preparation according to the invention or of the compositions according to the invention can also be coated or compounded in another way in order to provide a dose form with delayed release. Suitable coating means are inter alia polymeric acids and mixtures of polymeric acids with materials such as shellac, cetyl alcohol and/or cellulose acetate.

The amount of active ingredient to be administered to the patient varies and is dependent on the weight, age and history of illness of the patient and on the method of application, the indication and the severity of the disease. Conventionally 0.1 to 5,000 mg/kg, in particular 1 to 500 mg/kg, preferably 2 to 250 mg/kg of bodyweight of at least one compound according to the invention of general formula I are applied.

The following examples serve to describe the present invention in more detail.

EXAMPLES

The chemicals and solvents used were commercially obtained from one of the following suppliers: Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen; TCI, Japan; or produced by methods known generally in the prior art.

Chromatographic purification took place on a HPLC-RP-18 column from Macherey-Nagel; material NUCLEOSIL 100-3 $C_{18}$-HD approximately 100 mm (VarioPrep), internal diameter 21 mm; eluent water/methanol, gradient: 50–100 % in about 18 min, flow: 10 ml/min; detection: UV, Beckman 168 PDA.

General Instruction AAV (Semi-automated Synthesis)

A small round-bottomed tube made of glass (diameter 16 mm, length 125 mm) with a thread was provided with an agitator and closed by a screw lid with septum. The tube was placed in the agitator block adjusted to 20° C. The following reagents were then added in succession using a pipette:
1 ml of a solution of trifluoroacetic acid, 0.1 M, and heteroarylamine components II, 0.1 M, in acetonitrile;
1 ml of a 0.11 M solution of the aldehyde III in acetonitrile;
1 ml of a 0.3 M solution of the olefin IV in acetonitrile.

The reaction mixture was stirred for 10 hours at 20° C. in one of the agitator blocks. The reaction solution was then filtered off. The tube was rinsed twice with 1.5 ml of a 7.5% $NaHCO_3$ solution respectively.

The rack with the samples was placed manually onto the working up unit. 2 ml ethylacetate were added to the reaction mixture on a vortexer and shaken. The mixture was briefly centrifuged in the centrifuge to form the phase boundary. The phase boundary was detected visually and the organic phase pipetted off. In the next step 2 ml ethylacetate were added to the aqueous phase again, the mixture shaken, centrifuged and the organic phase pipetted off. The combined organic phases were dried over 2.4 g $MgSO_2$ (granulated). The solvent was removed in a vacuum centrifuge.

Each sample was characterized using ESI-MS and/or NMR. Mass spectrometric investigations (ESI-MS) were carried out using a mass spectrometer from Finnegan, LCQ Classic. $^1$H-NMR investigations of the compounds according to the invention were carried out using a 300 MHz DPX Advance NMR apparatus from Bruker.

Examples 1 to 61 (see Table 1) were produced in accordance with the cited AAV. Examples 43 to 45 were purified by means of reversed-phase HPLC.

TABLE 1

| Example | Calculated mass | Ascertained mass | Name |
|---|---|---|---|
| 1 | 366.37 | 367.3 | 4-(4-methoxy-phenyl)-3-methyl-2-(5-nitro--furan-2-yl)-3,4-dihydro-2H-pyrazino[1,2a]-pyrimidine |
| 2 | 367.44 | 368.4 | 2-[4-(4-methoxy-phenyl)-3-methyl-3,4-dihydro--2H-pyrazino[1,2a]pyrimidin-2-yl]-- cyclopropane carboxylic acid ethyl ester |
| 3 | 335.4 | 336.2 | 4-(4-methoxy-phenyl)-3-methyl-2-(5-methyl--furan-2-yl)-3,4-dihydro-2H-pyrazino[1,2a]-pyrimidine |
| 4 | 343.38 | 344.2 | 4-(3,4-dimethoxy-phenyl)-3,4-dihydro-2H--pyrazino[1,2a]pyrimidine-2--carboxylic acid ethyl ester |
| 5 | 313.35 | 314.1 | 4-(4-methoxy-phenyl)-3,4-dihydro-2H--pyrazino[1,2a]pyrimidine-2-carboxylic acid ethyl ester |
| 6 | 392.25 | 391.1/ 393.1 | 7-bromo-4-(4-methoxy-phenyl)-3,4-dihydro-2H--pyrimido[1,2a]pyrimidine-2-- carboxylic acid ethyl ester |
| 7 | 315.32 | 316.2 | 4-(3,4-dimethoxy-phenyl)-3,4-dihydro-2H--pyrimido[1,2a]pyrimidine-2-carboxylic acid |
| 8 | 394.22 | 393.2/ 395.1 | 7-bromo-4-(3,4-dimethoxy-phenyl)-3,4-dihydro--2H-pyrimido[1,2a]pyrimidine-2-carboxylic acid |
| 9 | 285.3 | 286.2 | 4-(4-methoxy-phenyl)-3,4-dihydro-2H--pyrazino[1,2a]pyrimidine-2-carboxylic acid |
| 10 | 364.2 | 363.2/ 365.0 | 7-bromo-4-(4-methoxy-phenyl)-3,4-dihydro-2H--pyrimido[1,2a]pyrimidine-2-carboxylic acid |
| 11 | 352.34 | 353.4 | 4-(4-methoxy-phenyl)-2-(5-nitro-furan-2-yl)-3,4-- dihydro 2H-pyrazino[1,2a]pyrimdine |
| 12 | 351.44 | 352.4 | 2-[4-(2,4-dimethyl-phenyl)-3,4-dihydro-2H--pyrazino[1,2a]pyrimidin-2-yl]-- cyclopropane carboxylic acid ethyl ester |
| 13 | 353.42 | 354.3 | 2-[4-(4-methoxy-phenyl)-3,4-dihydro-2H--pyrazino[1,2a]pyrimidin-2-yl]-- cyclopropane carboxylic acid ethyl ester |
| 14 | 313.35 | 314.3 | 4-(4-hydroxy-phenyl)-3-methyl-3,4-dihydro-2H--pyrazino[1,2a]pyrimidine-2--carboxylic acid ethyl ester |
| 15 | 392.25 | 391.4/ 393.0 | 7-bromo-4-(4-hydroxy-phenyl)-3-methyl-3,4-- dihydro-2H-pyrimido[1,2a]pyrimidine-2--carboxylic acid ethyl ester |
| 16 | 295.34 | 296.3 | 6,6a,7,11b-tetrahydro-3,5,11c-triaza-- benzo[c]fluorene-6-carboxylic acid ethyl ester |
| 17 | 374.24 | 373.3/ 375.3 | 2-bromo-6,6a,7,11b-tetrahydro-4,5,11c-triaza--benzo[c]fluoren-6-carboxylic acid ethyl ester |
| 18 | 315.39 | 316.3 | 4-phenylsulphanyl-3,4-dihydro-2H-pyrazino[1,2a]-pyriniidine-2-carboxylic acid ethyl ester |
| 19 | 287.34 | 288.2 | 4-phenylsulphanyl-3,4-dihydro-2H-pyrazino[1,2a]-pyrimidine-2-carboxylic acid |
| 20 | 299.32 | 300.2 | 4-(4-methoxy-phenyl)-3-methyl-3,4-dihydro--2H-pyrazino[1,2a]pyrimidine-2-carboxylic acid |
| 21 | 378.23 | 377.1/ 379.1 | 7-bromo-4-(4-methoxy-phenyl)-3-methyl-3,4--dihydro-2H-pyrimido[12a]pyrimidine-2-carboxylic acid |
| 22 | 315.32 | 316.2 | 4-(3,4-dimethoxy-phenyl)-3,4-dihydro-2H--pyrazino[1,2a]pyrimidine-2-carboxylic acid |
| 23 | 394.22 | 393.1/ 395.1 | 7-bromo-4-(3,4-dimethoxy-phenyl)-3,4-dihydro--2H-pyrimido[1,2a]pyrimidine-2-carboxylic acid |
| 24 | 285.3 | 286.2 | 4-(4-methoxy-phenyl)-3,4-dihydro-2H--pyrazino[1,2a]pyrimidine-2-carboxylic acid |
| 25 | 364.2 | 363.1/ 365.1 | 7-bromo-4-(4-methoxy-phenyl)-3,4-dihydro-2H--pyrimido[1,2a]pyrimidine-2-carboxylic acid |
| 26 | 299.32 | 300.2 | [4-(2-hydroxy-ethoxy)-3,4-dihydro-2H--pyrazino[1,2a]pyrimidin-2-yl]-phenyl-methanone |
| 27 | 378.23 | 379.1 | [7-bromo-4-(2-hydroxy-ethoxy)-3,4-dihydro-2H--pyrazino[1,2a]-pyrimidin-2-yl]-phenyl-methanone |
| 28 | 375.42 | 374.2/ 376.2 | [4-(4-hydroxy-3-methoxy-phenyl)-3-methyl-3,4-- dihydro-2H-pyrazino[1,2a]pyrimidin-2-yl]--phenyl-methanone |
| 29 | 454.32 | 451.2/ 453.1 | [7-bromo-4-(4-hydroxy-3-methoxy-phenyl)-3-methyl-3,4-dihydro-2H-pyrimido[1,2a]-pyrimidin-2-yl]-phenyl-methanone |

TABLE 1-continued

| Example | Calculated mass | Ascertained mass | Name |
|---|---|---|---|
| 30 | 359.42 | 360.2 | [4-(4-methoxy-phenyl)-3-methyl-3,4-dihydro--2H-pyrazino[1,2a]pyrimidin-2-yl]-phenyl-methanone |
| 31 | 438.32 | 437.1/ 439.1 | [7-bromo-4-(4-methoxy-phenyl)-3-methyl-3,4-- dihydro-2H-pyrimido[1,2a]pyrimidin-2-yl]--phenyl-metbanone |
| 32 | 345.4 | 345.2 | [4-(4-hydroxy-phenyl)-3-methyl-3,4-dihydro--2H-pyrazino[1,2a]pyrimidin-2-yl]-phenyl--methanone |
| 33 | 424.3 | 423.1/ 425.1 | [7-bromo-4-(4-hydroxy-phenyl)-3-methyl-3,4--dihydro-2H-pyrimido[1,2a]pyrimidin-2-yl]--phenyl-methanone |
| 34 | 454.32 | 453.2/ 455.1 | [7-bromo-4-(3,4-dimethoxy-phenyl)-3,4-dihydro-2H-pyrimido[1,2a]pyrimidin-2-yl]-phenyl--methanone |
| 35 | 424.3 | 423.2/ 425.1 | [7-bromo-4-(4-methoxy-phenyl)-3,4-dihydro-2H-pyrimido[1,2a]pyrimidin-2-yl]-phenyl-methanone |
| 36 | 314.18 | 313.1/ 315.1 | 2-(7-bromo-2-cyclopropyl-3,4-dihydro-2H--pyrimido[1,2a]pyrimidin-4-yloxy)-ethanol |
| 37 | 311.38 | 312.2 | 2-cyclopropyl-4-(3,4-dimethoxy-phenyl)-3,4-- dihydro-2H-pyrazino[1,2a]pyrimidine |
| 38 | 281.35 | 282.2 | 2-cyclopropyl-4-(4-methoxy-phenyl)-3,4-- dihydro-2H-pyrazino[1,2a]pyrimidine |
| 39 | 277.36 | 278.2 | 2-(2-cyclohexyl-3,4-dihydro-2H-pyrazmo[1,2a]-pyrimidm-4-yloxy)-ethanol |
| 40 | 356.26 | 357.2 | 2-(7-bromo-2-cyclohexyl-3,4-dihydro-2H--pyrimido[1,2a]pyrimidin-4-yloxy)-ethanol |
| 41 | 402.34 | 403.1 | 4-(7-bromo-2-cyclohexyl-3-methyl-3,4-dihydro-2H-pyrimido[1,2a]pyrimidin-4-yl)-phenol |
| 42 | 323.43 | 324.2 | 2-cyclohexyl-4-(4-methoxy-phenyl)-3,4--dihydro-2H-pyrazino[1,2a]pyrimidine |
| 43 | 412.29 | 413.1 | 7-bromo-4-naphthalin-2-yl-3,4-dihydro-2H--pyrimido[1,2a]pyrimidine-2--carboxylic acid ethyl ester |
| 44 | 376.25 | 375.4/ 377.4 | 7-bromo-4-m-tolyl-3,4-dihydro-2H-pyrimido-[1,2-a]pyrimidme-2-carboxylic acid ethyl ester |
| 45 | 430.35 | 431.1 | 2-[7-bromo-4-(2,4-dimethyl-phenyl)-3,4-dihydro--2H-pyrimido[1,2a]pyrimidin-2-yl]--cyclopropane carboxylic acid ethyl ester |
| 46 | 432.32 | 431.4/ 433.4 | 2-[7-bromo-4-(4-methoxy-phenyl)-3,4-dihydro--2H-pyrimido[1,2a]pyrimidin-2-yl]--cyclopropane carboxylic acid ethyl ester |
| 47 | 336.35 | 337.3 | 4-methyl-2-(5-nitro-furan-2-yl)-4-phenyl-3,4--dihydro-2H-pyrazino[1,2a]pyrimidine |
| 48 | 339.44 | 338.3 | 2-(4-methyl-4-phenyl-3,4-dihydro-2H--pyrazino[1,2a]pyrimidin-2-yl]--cyclopropane carboxylic acid ethyl ester |
| 49 | 320.41 | 321.2 | 4-phenylsulphanyl-2-pyridin-2-yl-3,4-dihydro-2H--pyrazino[1,2a]pyrimidine |
| 50 | 364.42 | 365.2 | 4-phenylsulphanyl-2-pyridin-2-yl-3,4-dihydro-2H--pyrazino[1,2a]pyrimidine-9-carboxylic acid |
| 51 | 412.9 | 413.3 | 6-Amino-7-chlor-4-phenylsulphanyl-2-pyridin-2--yl-3,4-dihydro-2H-pyrazino[1,2a]pyrimidin-9--carboxylic acid amide |
| 52 | 421.52 | 422.4 | 7-phenyl-4-phenylsulphanyl-2-pyridin-2-yl-3,4--dihydro-2H-pyrazino[1,2a]pyrimidine-9--carbonitrile |
| 53 | 343.23 | 343.2 | 7-bromo-4-phenylsulphanyl-2-pyridin-2-yl-3,4--dihydro-2H-pyrimido[1,2a]pyrimidine |
| 54 | 369.87 | 370.3 | 2-chloro-6-phenylsulphanyl-8-pyridin-2-yl-7,8--dihydro-6H-pyrimido[1,2a]pyrimidin-4-yl-amine |
| 55 | 352.41 | 353.3 | 6-phenylsulphanyl-8-pyridin-2-yl-7,8-dihydro-6H--pyrimido[1,2a]pyrimidin-2,4-diol |
| 56 | 460.48 | 461.3 | 6-phenylsulphanyl-8-pyridin-2-yl-2-trifluormethyl--7,8-dihydro-6H-pyrimido[1,2a]pyrimidine-3--carboxylic acid ethyl ester |
| 57 | 276.35 | 277.4 | 5,8-methano-9-pyridin-2-yl-5,8,84,9-tetrahydro--4bH-2,44,10-triaza-phenanthrene |
| 58 | 360.82 | 324.3 (M—Cl) | 1-chloro-5,8-methano-9-pyridin-2-yl-5,8,8a,9--tetrahydro-4bH-2,44,10-triaza-phenanthren-e-3,4-dicarbonitrile |
| 59 | 388.4 | 324.1 (M—COOH—OH) | 12-hydroxy-1,4-methano-5-pyridin-2-yl-1,4a,5,12b-etrahydro-4H-6,7,8,11,12a--pentaaza-benzo[a]anthracene-10-carboxylic acid |
| 60 | 322.36 | 323.2 | 3-methyl-5,8-methano-9-pyridin-2-yl-5,8,8a,9--tetrahydro-4bH-1,44,10-triaza-phenanthren-e-2,4-diol |
| 61 | 308.35 | 309.3 | 5,8-methano-9-pyridin-2-yl-5,8,84,9-tetrahydro--4bH-1,4a,10-triaza-phenanthrene-2,4-diol |
| 62 | 343.23 | 343.2 | 3-bromo-9-pyridin-2-yl-7,8,84,9-tetrahydro--4bH-1,44,10-triaza-phenanthrene |

Pharmacological Tests

Compounds according to the invention were investigated with respect to their pharmacological properties using methods described by J. P. Devlin in "High throughput screening—the discovery of bioactive substances," Marcel Dekker, New York, 1997, pages 275 to 453. The results of these tests are summarized in Tables 2 and 3, and demonstrate the analgesic efficacy of the compounds according to the invention.

TABLE 2

$K_i$ Value of the μ-opiate Receptor Bond

| Example | $K_i$ (μM) |
|---|---|
| 51 | 1.4 |
| 52 | 1.4 |
| 53 | 2.5 |

TABLE 3

% inhibition of NMDA/MK801-binding site

| Example | % inhibition (10 pM) |
|---|---|
| 51 | 40 |
| 52 | 47 |
| 53 | 44 |
| 61 | 40 |
| 62 | 40 |

Pharmaceutical Formulation of a Pharmaceutical Preparation According to the Invention 1 g of the hydrochloride of 4-(3,4-dimethoxy-phenyl)3,4-dihydro-2H-pyrazino[1,2a]pyrimide-2-carboxylic acid was dissolved in 1 l water at ambient temperature for injection purposes and subsequently adjusted to isotonic conditions by adding sodium chloride.

What is claimed is:

1. A compound of formula I

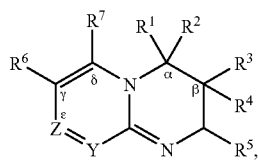

I wherein

Y represents $CR^8$ and

Z represents N;

$R^1$ and $R^2$ independently of one another represent H; $OR^{10}$; SH; $SR^{10}$; $C_{1-12}$ alkanyl, which is straight-chained or branched and unsubstituted or singly or multiply substituted; $C_{3-8}$ cycloalkyl, wherein the cycloalkyl is saturated and unsubstituted or singly or multiply substituted; heterocyclyl, wherein the heterocyclyl is 3-, 4-, 5-, 6- or 7-membered and is saturated and unsubstituted or singly or multiply substituted; aryl, wherein aryl is unsubstituted or singly or multiply substituted; heteroaryl, wherein the heteroaryl is unsubstituted or singly or multiply substituted; ($C_{1-6}$ alkanyl)-aryl, wherein the $C_{1-6}$ alkanyl is straight-chained or branched and unsubstituted or singly or multiply substituted and the aryl is unsubstituted or singly or multiply substituted; or ($C_{1-6}$ alkanyl)-heteroaryl, wherein the $C_{1-6}$ alkanyl is straight-chained or branched and unsubstituted or singly or multiply substituted and the heteroaryl is unsubstituted or singly or multiply substituted, wherein if one of $R^1$ and $R^2$ is H and the other of $R^1$ and $R^2$ is not H, and wherein if one of $R^1$ and $R^2$ represents aryl, the other of $R^1$ and $R^2$ represents H or $C_{1-12}$ alkanyl, $R^3$ and $R^4$ independently of one another represent H; $C_{1-12}$ alkanyl, wherein the $C_{1-12}$ alkanyl is straight-chained or branched and unsubstituted or singly or multiply substituted; $C_{3-8}$ cycloalkyl, wherein the cycloalkyl is saturated and unsubstituted or singly or multiply substituted; aryl, wherein the aryl is unsubstituted or singly or multiply substituted; heteroaryl, wherein the heteroaryl is unsubstituted or singly or multiply substituted; ($C_{1-6}$ alkanyl)-aryl, wherein the $C_{1-6}$ alkanyl is straight-chained or branched and unsubstituted or singly or multiply substituted and the aryl is unsubstituted or singly or multiply substituted; or ($C_{1-6}$ alkanyl)-heteroaryl, wherein the $C_{1-6}$ alkanyl is straight-chained or branched and unsubstituted or singly or multiply substituted and the heteroaryl is unsubstituted or singly or multiply substituted, wherein at least one of $R^3$ and $R^4$ is H, or $R^5$ represents $C_{1-12}$ alkanyl, which is straight-chained or branched, and unsubstituted or singly or multiply substituted; $C_{3-8}$ cycloalkyl, which is saturated and unsubstituted or singly or multiply substituted; heterocyclyl, wherein the heterocyclyl is 3-, 4-, 5-, 6- or 7-membered and is saturated and unsubstituted or singly or multiply substituted; aryl, which is unsubstituted or singly or multiply substituted; heteroaryl, which is unsubstituted or singly or multiply substituted; ($C_{1-6}$ alkanyl)-aryl, wherein the $C_{1-6}$ alkanyl is straight-chained or branched and unsubstituted or singly or multiply substituted and the aryl is unsubstituted or singly or multiply substituted; or ($C_{1-6}$ alkanyl)-heteroaryl, wherein $C_{1-6}$ alkanyl is straight-chained or branched and unsubstituted or singly or multiply substituted and heteroaryl is unsubstituted or singly or multiply substituted, $C(=O)R^{11}$, $CO_2H$ or $CO_2R^{12}$, $R^6$, $R^7$, and $R^8$ independently of one another represent H, F, Cl, Br, I, CN, $NH_2$, $NH(C_{1-6}$ alkyl), $N(C_{1-6}$ alkyl)$_2$, $NH((C_{1-6}$ alkyl)-aryl), $N((C_{1-6}$ alkyl)-aryl)$_2$, NH-aryl, $N(aryl)_2$, $NHR^{13}$, $NO_2$, OH, SH; O—$C_{1-8}$ alkyl or $S(O)_p$—$C_{1-8}$ alkyl, wherein the alkyl is straight-chained or branched and unsubstituted or singly or multiply substituted and p is 0, 1 or 2; O-aryl or $S(O)_q$ aryl, wherein the aryl is unsubstituted or singly or multiply substituted and q is 0, 1 or 2; O—($C_{1-6}$ alkyl)-aryl or $S(O)_r$—($C_{1-6}$ alkyl)-aryl, wherein the $C_{1-6}$ alkyl is straight-chained or branched and unsubstituted or singly or multiply substituted and the aryl is unsubstituted or singly or multiply substituted and r is 0, 1 or 2; $CO_2H$, $C(=O)R^{14}$; $C_{1-12}$ alkyl, wherein the alkyl is straight-chained or branched and unsubstituted or singly or multiply substituted; $CF_3$; $C_{3-8}$ cycloalkyl, wherein the cycloalkyl is saturated or unsaturated and unsubstituted or singly or multiply substituted; heterocyclyl, which is 3-, 4-, 5-, 6- or 7-membered and is saturated or unsaturated and unsubstituted or singly or multiply substituted; aryl, wherein the aryl is unsubstituted or singly or multiply substituted; or heteroaryl, wherein the heteroaryl is unsubstituted or singly or multiply substituted, or

23

R$^{10}$ represents C$_{1-8}$ alkanyl, which is straight-chained or branched and unsubstituted or singly or multiply substituted; C$_{3-8}$ cycloalkyl, which is saturated and unsubstituted or singly or multiply substituted; heterocyclyl, which is 3-, 4-, 5-, 6- or 7-membered and is saturated and unsubstituted or singly or multiply substituted; aryl, which is unsubstituted or singly or multiply substituted; heteroaryl, which is unsubstituted or singly or multiply substituted; (C$_{1-6}$ alkanyl)-aryl, wherein the C$_{1-6}$ alkanyl is straight-chained or branched and unsubstituted or singly or multiply substituted, and the aryl is unsubstituted or singly or multiply substituted; or (C$_{1-6}$ alkanyl)-heteroaryl, wherein the C$_{1-6}$ alkanyl is straight-chained or branched and unsubstituted or singly or multiply substituted and the heteroaryl is unsubstituted or singly or multiply substituted, R$^{11}$ represents NH$_2$, NH(C$_{1-6}$ alkanyl), N(C$_{1-6}$ alkanyl)$_2$, NH((C$_{1-6}$ alkanyl)-aryl), N((C$_{1-8}$ alkanyl)-aryl)$_2$, NH-aryl, N(aryl)$_2$, C$_{1-6}$ alkanyl, wherein the alkanyl is straight-chained or branched and unsubstituted or singly or multiply substituted; C$_{3-8}$ cycloalkyl, wherein the cycloalkyl is saturated and unsubstituted or singly or multiply substituted; aryl, which is unsubstituted or singly or multiply substituted; heteroaryl, which is unsubstituted or singly or multiply substituted; (C$_{1-6}$ alkanyl)-aryl, wherein the C$_{1-6}$ alkanyl is straight-chained or branched and unsubstituted or singly or multiply substituted and the aryl is unsubstituted or singly or multiply substituted; or (C$_{1-6}$ alkanyl)-heteroaryl, wherein the C$_{1-6}$ alkanyl is straight-chained or branched and unsubstituted or singly or multiply substituted and the heteroaryl is unsubstituted or singly or multiply substituted, R$^{12}$ represents C$_{1-8}$ alkanyl, wherein the alkanyl is straight-chained or branched and unsubstituted or singly or multiply substituted; C$_{3-8}$ cycloalkyl, wherein the cycloalkyl is saturated and unsubstituted or singly or multiply substituted; (C$_{1-6}$ alkanyl)-aryl, wherein the C$_{1-6}$ alkanyl is straight-chained or branched and unsubstituted or singly or multiply substituted and the aryl is unsubstituted or singly or multiply substituted, R$^{13}$ represents C(=O)CH$_3$, C(=O) phenyl or C(=O)O-t.-butyl(t-BOC), R$^{14}$ represents H, NH$_2$, NH(C$_{1-6}$ alkyl), N(C$_{1-6}$ alkyl)$_2$, NH((C$_{1-6}$ alkyl)-aryl), N((C$_{1-6}$ alkyl)-aryl)$_2$, NH-aryl, N(aryl)$_2$, C$_{1-8}$ alkyl, wherein the alkyl is straight-chained or branched and unsubstituted or singly or multiply substituted; C$_{3-8}$ cycloalkyl, which is saturated or unsaturated and unsubstituted or singly or multiply substituted; aryl, which is unsubstituted or singly or multiply substituted; (C$_{1-6}$ alkyl)-aryl, wherein the C$_{1-6}$ alkyl is straight-chained or branched and unsubstituted or singly or multiply substituted, and the aryl is unsubstituted or singly or multiply substituted; OC$_{1-8}$ alkyl, wherein the alkyl is straight-chained or branched and unsubstituted or singly or multiply substituted; OC$_{3-8}$ cycloalkyl wherein the cycloalkyl is saturated or unsaturated and unsubstituted or singly or multiply substituted; O-aryl, wherein the aryl is unsubstituted or singly or multiply substituted, or O—(C$_{1-6}$ alkyl)-aryl, wherein the C$_{1-6}$ alkyl is straight-chained or branched and unsubstituted or singly or multiply substituted, and the aryl is unsubstituted or singly or multiply substituted, R$^{15}$, R$^{16}$, R$^{17}$ and R$^{18}$ independently of one another represent H, F, Cl, Br, I, OH, ON; C$_{1-8}$ alkyl, wherein

24 alkyl is straight-chained or branched and unsubstituted or singly or multiply substituted; or CO$_2$H, and or a pharmaceutically acceptable salt thereof.

2. A compound according to claim 1, in the form of a racemate or a pure enantiomer.

3. A compound according to claim 1, in the form of a mixture of enantiomers, or in the form of a mixture of diastereomers.

4. A compound according to claim 2, wherein

Y represents CR$^8$,

Z represents N, one of R$^1$ and R$^2$ represents OR$^{10}$, SR$^{10}$, C$_{1-6}$ alkanyl or aryl, R$^3$ and R$^4$ represents H or C$_{1-6}$ alkanyl, or R$^5$ represents C$_{3-7}$ cycloalkyl, heteroaryl, C(=O)R$^{11}$, CO$_2$H or CO$_2$R$^{12}$, R$^6$ represents H, F, Cl, Br, CN, NO$_2$, C(=O)R$^{14}$, C$_{1-6}$ alkyl, CF$_3$ or aryl, R$^7$ represents H, F, Cl, Br, CN, NH$_2$, OH or C$_{1-6}$ alkyl, R$^8$ represents H, F, Cl, Br, CN, NO$_2$, O—(C$_{1-6}$ alkyl)-aryl, CO$_2$H, CONH$_2$ or C$_{1-6}$ alkyl, R$^{10}$ represents C$_{1-8}$ alkanyl or aryl, R$^{11}$ represents aryl, R$^{12}$ represents C$_{1-6}$ alkanyl and R$^{14}$ represents OC$_{1-6}$ alkyl.

5. A compound according to claim 4, wherein one of R$^1$ and R$^2$ represents O—(CH$_2$)$_2$—OH, S-phenyl, phenyl, 3-methylphenyl, 2,4-dimethylphenyl, 4-hydroxyphenyl, 4-methoxyphenyl, 4-hydroxy-3-methoxyphenyl or 3,4-dimethoxyphenyl, one of R$^3$ and R$^4$ represents H or methyl, R$^5$ represents cyclopropyl, 2-(C(=O)O-ethyl)-cyclopropyl, cyclohexyl, 2-pyridinyl, 5-methyl-furan-2-yl, 5-nitro-furan-2-yl, C(=O) phenyl, CO$_2$H or CO$_2$ ethyl, R$^6$ represents H, Cl, CN or phenyl, R$^7$ represents H, NH$_2$ or CN and R$^8$ represents H, Cl, CN, CO$_2$H or CONH$_2$.

6. A compound according to claim 4, selected from the group consisting of:

4-(4-methoxy-phenyl)-3-methyl-2-(5-nitro-furan-2-yl)-3,4-dihydro-2H-pyrazino[1,2a]pyrimidine, 2-[4-(4-methoxy-phenyl)-3-methyl-3,4-dihydro-2H-pyrazino[1,2a]pyrimidin-2-yl]-cyclopropane carboxylic acid ethyl ester, 4-(4-methoxy-phenyl)-3-methyl-2-(5-methyl-furan-2-yl)-3,4-dihydro-2H-pyrazino[1,2a]pyrimidine, 4-(3,4-dimethoxy-phenyl)-3,4-dihydro-2H-pyrazino[1,2a]pyrimidine-2-carboxylic acid ethyl ester, 4-(4-methoxy-phenyl)-3,4-dihydro-2H-pyrazino[1,2a]pyrimidine-2-carboxylic acid ethyl ester, 4-(3,4-dimethoxy-phenyl)-3,4-dihydro-2H-pyrazino[1,2a]pyrimidine-2-carboxylic acid, 4-(4-methoxy-phenyl)-3,4-dihydro-2H-pyrazino[1,2a]pyrimidine-2-carboxylic acid, 4-(4-methoxy-phenyl)-2-(5-nitro-furan-2-yl)-3,4-dihydro-2H-pyrazino[1,2a]pyrimidine, 2-[4-(2,4-dimethyl-phenyl)-3,4-dihydro-2H-pyrazino[1,2a]pyrimidin-2-yl]-cyclopropane carboxylic acid ethyl ester, 2-[4-(4-methoxy-phenyl)-3,4-dihydro-2H-pyrazino[1,2a]pyrimidin-2-yl]cyclopropane carboxylic acid ethyl ester, 4-(4-hydroxy-phenyl)-3-methyl-3,4-dihydro-2H-pyrazino[1,2-a]pyrimidine-2-carboxylic acid ethyl ester, 4-phenylsulphanyl-3,4-dihydro-2H-pyrazino[1,2a]pyrimidine-2-carboxylic acid ethyl ester, 4-phenylsulphanyl-3,4-dihydro-2H-pyrazino[1,2a]pyrimidine-2-carboxylic acid, 4-(4-methoxy-phenyl)-3-methyl-3,4-dihydro-2H-pyrazino[1,2-a]pyrimidine-2-carboxylic acid,
4-(3,4-dimethoxy-phenyl)-3,4-dihydro-2H-pyrazino[1,2a]pyrimidine-2-carboxylic acid,
4-(4-methoxy-phenyl)-3,4-dihydro-2H-pyrazino[1,2a]pyrimidine -2-carboxylic acid,
[4-(2-hydroxy-ethoxy)-3,4-dihydro-2H-pyrazino[1,2a]pyrimidin-2-yl]-phenyl-methanone,
[4-(4-hydroxy-3-methoxy-phenyl)-3-methyl-3,4-dihydro-2H-pyrazino[1,2a]pyrimidin-2-yl]-phenyl-methanone,
[4-(4-methoxy-phenyl)-3-methyl-3,4-dihydro-2H-pyrazino[1,2-a]pyrimidin-2-yl]-phenyl-methanone,
[4-(4-hydroxy-phenyl)-3-methyl-3,4-dihydro-2H-pyrazino[1,2-a]pyrimidin-2-yl]-phenyl-methanone,
2-cyclopropyl-4-(3,4-dimethoxy-phenyl)-3,4-dihydro-2H-pyrazino[1,2a]pyrimidine,
2-cyclopropyl-4-(4-methoxy-phenyl)-3,4-dihydro-2H-pyrazino[1,2a]pyrimidine,
2-(2-cyclohexyl-3,4-dihydro-2H-pyrazino[1,2a]pyrimidin-4-yloxy)ethanol,
2-cyclohexyl-4-(4-methoxy-phenyl)-3,4-dihydro-2H-pyrazino[1,2a]pyrimidine,
4-methyl-2-(5-nitro-furan-2-yl)-4-phenyl-3,4-dihydro-2H-pyrazino[1,2a]pyrimidine,
2-(4-methyl-4-phenyl-3,4-dihydro-2H-pyrazino[1,2a]pyrimidin-2-yl)cyclopropane carboxylic acid ethyl ester,
4-phenyl-2-pyridin-2-yi-3,4-dihydro-2H-pyrazino[1,2a]pyrimidine,
4-phenyl-2-pyridin-2-yl-3,4-dihydro-2H-pyrazino[1,2a]pyrimidine-9-carboxylic acid,
6-amino-7-chloro-4-phenyl-2-pyridin-2-yl-3,4-dihydro-2H-pyrazino[1,2a]pyrimidine-9-carboxylic acid amide,
4-phenylsulphanyl-2-pyridin-2-yl-3,4-dihydro-2H-pyrazino[1,2-a]pyrimidine-9-carboxylic acid,
6-amino-7-chloro-4-phenylsulphanyl-2-pyridin-2-yl-3,4-dihydro-2H-pyrazino[1,2a]pyrimidine-9-carboxylic acid amide, and
7-phenyl-4-phenylsulphanyl-2-pyridin-2-yl-3,4-dihydro-2H-pyrazino[1,2a]pyrimidine -9-carbonitrile.

7. A method for producing a compound of according to claim 1, comprising
reacting a heteroarylamine of formula II

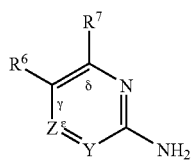

wherein Y, Z, $R^6$ and $R^7$ are as defined for formula I, with an aldehyde of formula III

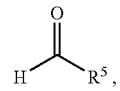

wherein $R^5$ is as defined for formula I,
and an olefin of formula IV

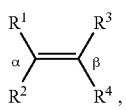

wherein $R^1$, $R^2$, $R^3$ and $R^4$ are as defined for formula I, in the presence of an acid.

8. A method according to claim 6, wherein the heteroarylamine of formula II is reacted with the aldehyde of formula III and the olefin of formula IV by a one pot method.

9. A method according to claim 7, wherein the acid is trifluoroacetic acid.

10. A method according to claim 8, wherein the reaction is carried out in an organic solvent at a temperature of 0 to 100° C. with a reaction time of 0.25 to 12 h.

11. A method according to claim 9, wherein the reaction is carried out at a temperature of 15 to 40° C.

12. A method according to claim 10, wherein the organic solvent is acetonitrile.

13. A substance library comprising at least one compound of claim 1.

14. A pharmaceutical composition comprising one or more compound of claim 1 and a pharmaceutically acceptable excipient.

15. A method for treating pain in a mammal, comprising administering to a mammal in need thereof an effective amount of the pharmaceutical composition of claim 14.

16. A method according to claim 15, wherein the mammal is human.

17. A method for treating at least one condition selected from the group consisting of urinary incontinence, itching, tinnitus, aurium and diarrhea in a mammal, comprising administering to a mammal in need thereof a therapeutically effective amount of a pharmaceutical composition of claim 14.

18. A method according to claim 17, wherein the mammal is human.

* * * * *